US012380537B2

(12) United States Patent
Trout et al.

(10) Patent No.: US 12,380,537 B2
(45) Date of Patent: Aug. 5, 2025

(54) 2D AND 3D COLOR FUSION IMAGING

(71) Applicant: DUKE UNIVERSITY, Durham, NC (US)

(72) Inventors: Robert Trout, Durham, NC (US); Joseph Izatt, Durham, NC (US); Christian B. Viehland, Durham, NC (US); Cynthia Toth, Durham, NC (US); Anthony Kuo, Durham, NC (US); Jianwei Li, Durham, NC (US); Lejla Vajzovic, Durham, NC (US); Al-Hafeez Dhalla, Durham, NC (US)

( * ) Notice: Subject to any disclaimer, the term of this patent is extended or adjusted under 35 U.S.C. 154(b) by 456 days.

(21) Appl. No.: 17/741,961

(22) Filed: May 11, 2022

(65) Prior Publication Data

US 2022/0366551 A1 Nov. 17, 2022

Related U.S. Application Data

(60) Provisional application No. 63/186,984, filed on May 11, 2021.

(51) Int. Cl.
*G06T 5/50* (2006.01)
*A61B 6/00* (2006.01)
*A61B 6/46* (2024.01)

(52) U.S. Cl.
CPC ............... *G06T 5/50* (2013.01); *A61B 6/466* (2013.01); *A61B 6/481* (2013.01); *G06T 2207/20221* (2013.01); *G06T 2207/30041* (2013.01)

(58) Field of Classification Search
CPC .................. A61B 6/466; A61B 6/481; G06T 2207/10024; G06T 2207/10101;
(Continued)

(56) References Cited

U.S. PATENT DOCUMENTS

2009/0009715 A1* 1/2009 Mensink ............... A61B 3/1025
351/221
2017/0119242 A1* 5/2017 Jia ....................... A61B 3/1005
(Continued)

OTHER PUBLICATIONS

Li Y, Gregori G, Knighton RW, Lujan BJ, Rosenfeld PJ. Registration of OCT fundus images with color fundus photographs based on blood vessel ridges. Opt Express. Jan. 3, 2011;19(1):7-16. doi: 10.1364/OE.19.000007. PMID: 21263537; PMCID: PMC3368356. (Year: 2011).*

(Continued)

*Primary Examiner* — Ian L Lemieux
(74) *Attorney, Agent, or Firm* — Talem IP Law, LLP

(57) ABSTRACT

A method of fusing 2D and 3D imaging data includes receiving 3D imaging data and 2D color imaging data of a region of interest, segmenting the 3D imaging data to identify anatomical features in the region of interest, including surfaces of the anatomical features and a corresponding volume of the anatomical features, and generating an image by fusing the 2D color imaging data to the 3D imaging data according to the surfaces, the corresponding volumes, and identities of the anatomical features. In some cases, the 3D imaging data is captured via optical coherence tomography. In some cases, the 2D color imaging data is captured via color microscopy. In some cases, the method further includes rendering a final image at an output plane by casting a ray through the fused 3D imaging data for each pixel and viewpoint of the output image plane for the image.

20 Claims, 6 Drawing Sheets

(58) Field of Classification Search
CPC .. G06T 2207/20221; G06T 2207/30041; G06T 5/50; G06T 7/11
See application file for complete search history.

(56) References Cited

U.S. PATENT DOCUMENTS

| | | | |
|---|---|---|---|
| 2018/0168737 A1* | 6/2018 | Ren | A61B 90/36 |
| 2018/0263490 A1* | 9/2018 | Jia | G06F 18/23 |
| 2018/0270474 A1* | 9/2018 | Liu | A61B 6/5247 |
| 2021/0353142 A1* | 11/2021 | Zhang | A61B 3/14 |
| 2022/0104884 A1* | 4/2022 | Leiderman | G06T 7/11 |
| 2022/0117696 A1* | 4/2022 | Shi | A61B 90/30 |
| 2024/0081642 A1* | 3/2024 | Toth | A61B 3/1225 |

OTHER PUBLICATIONS

Chaoqing Xu, Guodao Sun, Ronghua Liang, A survey of volume visualization techniques for feature enhancement, Visual Informatics, vol. 5, Issue 3, 2021, pp. 70-81, ISSN 2468-502X, https://doi.org/10.1016/j.visinf.2021.08.001. (Year: 2021).*
Tom McReynolds, David Blythe, Chapter 20—Scientific Visualization, In The Morgan Kaufmann Series in Computer Graphics, Advanced Graphics Programming Using OpenGL, Morgan Kaufmann, 2005, pp. 531-570, ISBN 9781558606593, https://doi.org/10.1016/B978-155860659-3.50022-6. (Year: 2005).*
Subramanian, M. L., et al., "Controversies in the Management of Primary Retinal Detachments:," International Ophthalmology Clinics, 2004, pp. 103-114, vol. 44, issue 4.
Carrasco-Zevallos O., et al., "Real-time 4D visualization of surgical maneuvers with 100kHz swept-source Microscope Integrated Optical Coherence Tomography (MIOCT) in model eyes," Investigative Ophthalmology & Visual Science, Apr. 30, 2014, 3 pages, vol. 55, issue 13.
Carrasco-Zevallos, O., et al., "4D microscope-integrated OCT improves accuracy of ophthalmic surgical maneuvers," Proceedings of SPIE: Ophthalmic Technologies XXVI, Mar. 4, 2016, 7 pages, vol. 9693, article 969306, SPIE, San Francisco, California.
Viehland, C., et al., "Enhanced volumetric visualization for real time 4D intraoperative ophthalmic swept-source OCT," Biomedical Optics Express, May 1, 2016 (accessible Apr. 12, 2016), p. 1815-29, vol. 7, issue 5.
Gorczynska, I., et al., "Projection OCT fundus imaging for visualising outer retinal pathology in non-exudative age-related macular degeneration," British Journal of Ophthalmology, May 1, 2009, 12 pages, vol. 93, issue 5.
Viehland, C., et al., "High Speed Volumetric Intrasurgical Optical Coherence Tomography at 400 kHz with Real Time, 4D Visualization of Surgical Maneuvers," Investigative Ophthalmology & Visual Science, Jun. 10, 2020, 2 pages, vol. 61, issue 7.
Abramoff, M. D., et al., "Retinal Imaging and Image Analysis," IEEE Reviews in Biomedical Engineering, Jan. 1, 2010, 96 pages, vol. 3.
Chiu, S. J., et al., "Automatic segmentation of seven retinal layers in SDOCT images congruent with expert manual segmentation," Optics Express, Aug. 27, 2010, p. 19413-428, vol. 18, issue 18.
Borkovkina, S., et al., "Real-time retinal layer segmentation of OCT volumes with GPU accelerated inferencing using a compressed, low-latency neural network," Biomedical Optics Express, Jul. 1, 2020 (Accessible Jun. 24, 2020), p. 3968-984, vol. 11, issue 7.
Viola, I., et al., "Importance-Driven Focus of Attention," IEEE Transactions on Visualization and Computer Graphics, Apr. 2006, 13 pages, vol. 12, issue 5.
Malzbender, T., "Fourier volume rendering," ACM Transactions on Graphics (TOG), Jul. 1993, pp. 233-250, vol. 12, issue 3, ACM New York, NY, USA.
Westover, L., "Interactive vol. rendering," Proceedings of the 1989 Chapel Hill Workshop on Volume Visualization, May 1989, pp. 9-16.
Viola, I., et al., "Importance-driven volume rendering," IEEE Visualization 2004, Oct. 10, 2004, 7 pages, IEEE Comput. Soc, Austin, TX, USA.
Todorich, B., et al., "Impact of Microscope-Integrated OCT on Ophthalmology Resident Performance of Anterior Segment Surgical Maneuvers in Model Eyes," Investigative Opthalmology & Visual Science, Jul. 13, 2016, p. OCT146-OCT153, vol. 57, issue 9.
Grewal, D. S., et al., "Intraoperative 4-Dimensional Microscope-Integrated Optical Coherence Tomography-Guided 27-Gauge Transvitreal Retinochoroidal Biopsy for Choroidal Melanoma," Retina, Apr. 2017, 9 pages, vol. 37, issue 4.
Carrasco-Zevallos, O. M., et al., "Optical Coherence Tomography for Retinal Surgery: Perioperative Analysis to Real-Time Four-Dimensional Image-Guided Surgery," Investigative Opthalmology & Visual Science, Jul. 13, 2016, p. OCT37-50, vol. 57, issue 9.
Carrasco-Zevallos, O. M., et al., "Live volumetric (4D) visualization and guidance of in vivo human ophthalmic surgery with intraoperative optical coherence tomography," Scientific Reports, Aug. 19, 2016, 16 pages, vol. 6, issue 1, article 31689.
Pasricha, N. D., et al., "Four-dimensional microscope-integrated optical coherence tomography to enhance visualization in glaucoma surgeries," Indian Journal of Ophthalmology, Jan. 2017, p. 57-59, vol. 65, issue 1.
Carrasco-Zevallos, O. M., et al., "Review of intraoperative optical coherence tomography: technology and applications [Invited]," Biomedical Optics Express, Mar. 1, 2017 (Accessible Feb. 21, 2017), p. 1607-1637, vol. 8, issue 3.
Lu, C. D., et al., "Microscope-Integrated Intraoperative Ultrahigh-Speed Swept-Source Optical Coherence Tomography for Widefield Retinal and Anterior Segment Imaging," Ophthalmic Surgery, Lasers and Imaging Retina, Feb. 1, 2018 (Accessible: Jan. 29, 2018), 15 pages, vol. 49, issue 2.
Seider, M. I., et al., "Real-Time Volumetric Imaging of Vitreoretinal Surgery with a Prototype Microscope-Integrated Swept-Source OCT Device," Ophthalmology Retina, May 1, 2018 (accessible: Nov. 8, 2017), 10 pages, vol. 2, issue 5.
Kolb, J. P., et al., "Live video rate volumetric OCT imaging of the retina with multi-MHz A-scan rates," Plos One, Mar. 28, 2019, 20 pages, vol. 14, issue 7, article e0220829.
Pujari, A., et al., "Intraoperative Optical Coherence Tomography Guided Ocular Surgeries: Critical Analysis of Clinical Role and Future Perspectives," Clinical Ophthalmology, Aug. 24, 2020, pp. 2427-2440, vol. 14.
Laíns, Inês, et al., "Retinal applications of swept source optical coherence tomography (OCT) and optical coherence tomography angiography (OCTA)," Progress in Retinal and Eye Research, Sep. 2021 (accessible: Jan. 28, 2021), 52 pages, vol. 84, article 100951.
Pujari, A., et al. "Clinical role of swept source optical coherence tomography in anterior segment diseases: a review," Seminars in Ophthalmology, Nov. 17, 2021 (accessible Mar. 10, 2021), 9 pages, vol. 36, issue 8.
Britten, A., et al., "Surgical microscope integrated MHz SS-OCT with live volumetric visualization," Biomedical Optics Express, Feb. 1, 2023 (Accessible Jan. 23, 2023), p. 846-65, vol. 14, issue 2.
Li, J. D., et al., "Intraoperative optical coherence tomography with 4D visualization of surgical maneuvers and quantitative measurements of intraocular structures," (Presentation, Abstract Only), Proceedings of SPIE: Ophthalmic Technologies XXXII, Mar. 7, 2022, presentation PC11947, 1 page, SPIE, San Francisco, United States.
Shen, L., et al., "Novel microscope-integrated stereoscopic display for intrasurgical optical coherence tomography," SPIE Proceedings: Ophthalmic Technologies XXV, Mar. 20, 2015, 6 pages, vol. 9307, article 930706, SPIE, San Francisco, California, United States.
Draelos, M., et al., "Real-time visualization and interaction with static and live optical coherence tomography volumes in immersive virtual reality," Biomedical Optics Express, Jun. 1, 2018 (Accessible May 30, 2018), pp. 2825-2843, vol. 9, issue 6.
Li, Y., et al., "Registration of OCT fundus images with color fundus photographs based on blood vessel ridges," Optics Express, Jan. 17, 2011 (Accessible Dec. 20, 2010), p. 7-16, vol. 19, issue 1.
Padmasini, N., et al., "Detection of neovascularisation using K-means clustering through registration of peripapillary OCT and fundus

(56) References Cited

OTHER PUBLICATIONS retinal images," 2016 IEEE International Conference on Computational Intelligence and Computing Research (ICCIC), Dec. 2016, 4 pages, IEEE, Chennai.
Dehghani, S., et al., "Robotic Navigation Autonomy for Subretinal Injection via Intelligent Real-Time Virtual iOCT Volume Slicing," Jan. 17, 2023, 8 pages, arXiv.
Sommersperger, M., et al., "Real-time tool to layer distance estimation for robotic subretinal injection using intraoperative 4D OCT," Biomedical Optics Express, Feb. 1, 2021 (accessible Jan. 27, 2021), pp. 1085-1104, vol. 12, issue 2.
Gende, M., et al., "End-to-end multi-task learning approaches for the joint epiretinal membrane segmentation and screening in OCT images," Computerized Medical Imaging and Graphics, Jun. 2022 (accessible: Apr. 25, 2022), 13 pages, vol. 98, article 102068.
Gende, M., et al., "Automatic Segmentation and Intuitive Visualisation of the Epiretinal Membrane in 3D OCT Images Using Deep Convolutional Approaches," IEEE Access, May 21, 2021, pp. 75993-6004, vol. 9, IEEE.
Mendes, O. L. C., et al., "Automatic Segmentation of Macular Holes in Optical Coherence Tomography Images: A review," Journal of Artificial Intelligence and Systems, Jan. 17, 2020, pp. 163-185, vol. 1, issue 1.
Stankiewicz, A., et al., "Novel full-automatic approach for segmentation of epiretinal membrane from 3D OCT images," 2017 Signal Processing: Algorithms, Architectures, Arrangements, and Applications (SPA), Sep. 20, 2017, 23 pages, IEEE, Poznan, Poland.
Hart, S. G., et al., "Development of NASA-TLX (Task Load Index): Results of Empirical and Theoretical Research," Advances in Psychology, 1988, pp. 139-183, vol. 52, Elsevier.
Rossi, J. V., et al., "Virtual Vitreoretinal Surgical Simulator as a Training Tool," Retina, Apr. 2004, pp. 231-236, vol. 24, issue 2.
Miri, M. S., et al., "Multimodal registration of SD-OCT volumes and fundus photographs using histograms of oriented gradients," Biomedical Optics Express, Dec. 1, 2016 (Accessible Nov. 23, 2016), p. 5252-67, vol. 7, issue 12.
Carrasco-Zevallos, O., et al., "Microscope-integrated OCT at 800 kHz line rate for high speed 4D imaging of ophthalmic surgery," (Abstract), Investigative Ophthalmology & Visual Science, May 7, 2017, 2 pages, vol. 58, issue 8.
Gabr, H., et al., "Visualization from intraoperative swept-source microscope-integrated optical coherence tomography in vitrectomy for complications of proliferative diabetic retinopathy," Retina, Sep. 1, 2018, 20 pages, vol. 38, supplement 1.
Vajzovic, L., et al., "Four-Dimensional Microscope-Integrated Optical Coherence Tomography (4D Mioct) Guidance in a Model Eye Subretinal Surgery," Retina, Oct. 5, 2019, 10 pages, vol. 39, supplement 1.
Toth, C. A., et al., "Surgically integrated swept source optical coherence tomography (SSOCT) to guide vitreoretinal (VR) surgery," (Abstract), Investigative Ophthalmology & Visual Science, Jun. 2015, 2 pages, vol. 56, issue 7.
Carrasco-Zevallos, O., et al., "Real-time 4D Stereoscopic Visualization of Human Ophthalmic Surgery with Swept-Source Microscope Integrated Optical Coherence Tomography," (Abstract), Investigative Ophthalmology & Visual Science, Jun. 2015, 3 pages, vol. 56, issue 7.
Bhullar, P. K., et al., "4D Microscope-Integrated OCT to Visualize Depth-Related Steps During Anterior Segment and External Eye Procedures," (Abstract), Investigative Ophthalmology & Visual Science, Sep. 26, 2016, 3 pages, vol. 57, issue 12.
Vajzovic, L., et al., "Subretinal Therapy Delivery Technique Guided by Intraoperative 4-Dimensional Microscope-Integrated Optical Coherence Tomography," (Abstract), Investigative Ophthalmology & Visual Science, Jun. 23, 2017, 6 pages, vol. 58, issue 8.
Viehland, C., et al. "High Speed Volumetric Intrasurgical Optical Coherence Tomography at 400 kHz with Real Time, 4D Visualization of Surgical Maneuvers," (Abstract), Investigative Ophthalmology & Visual Science, Jun. 10, 2020, 3 pages, vol. 61, issue 7.

\* cited by examiner

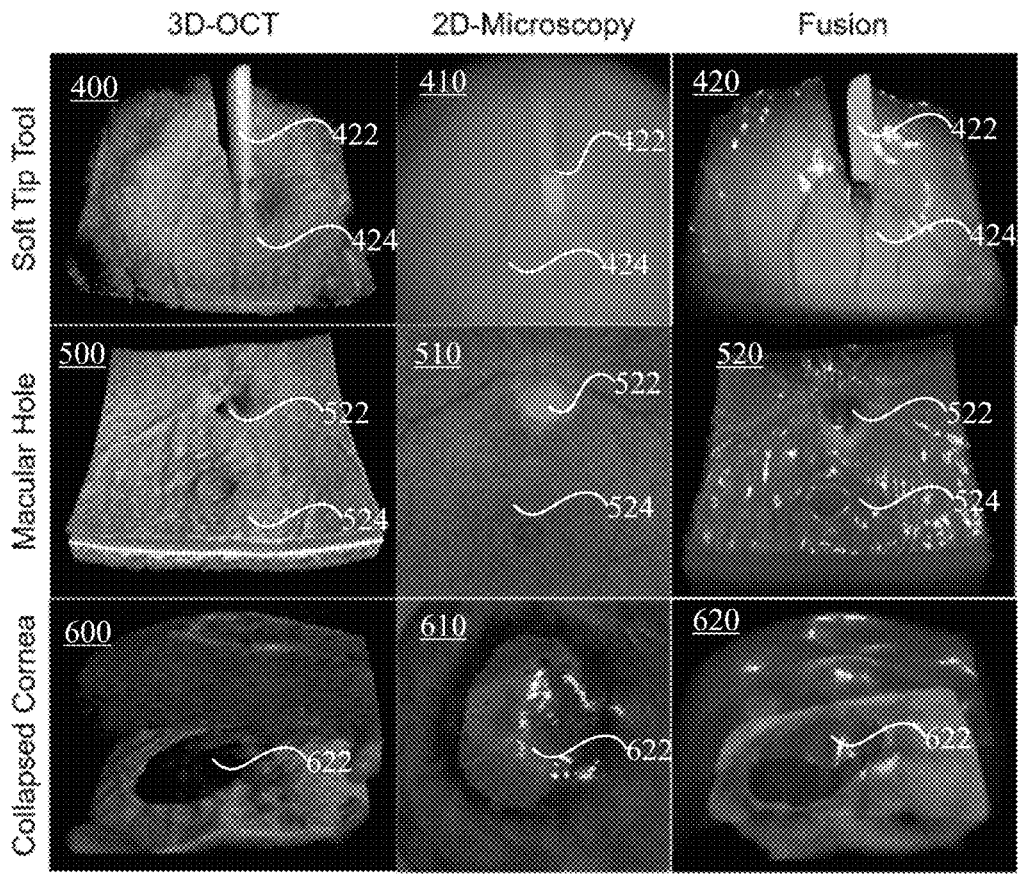
Figures 4A-4C
Figures 5A-5C
Figures 6A-6C
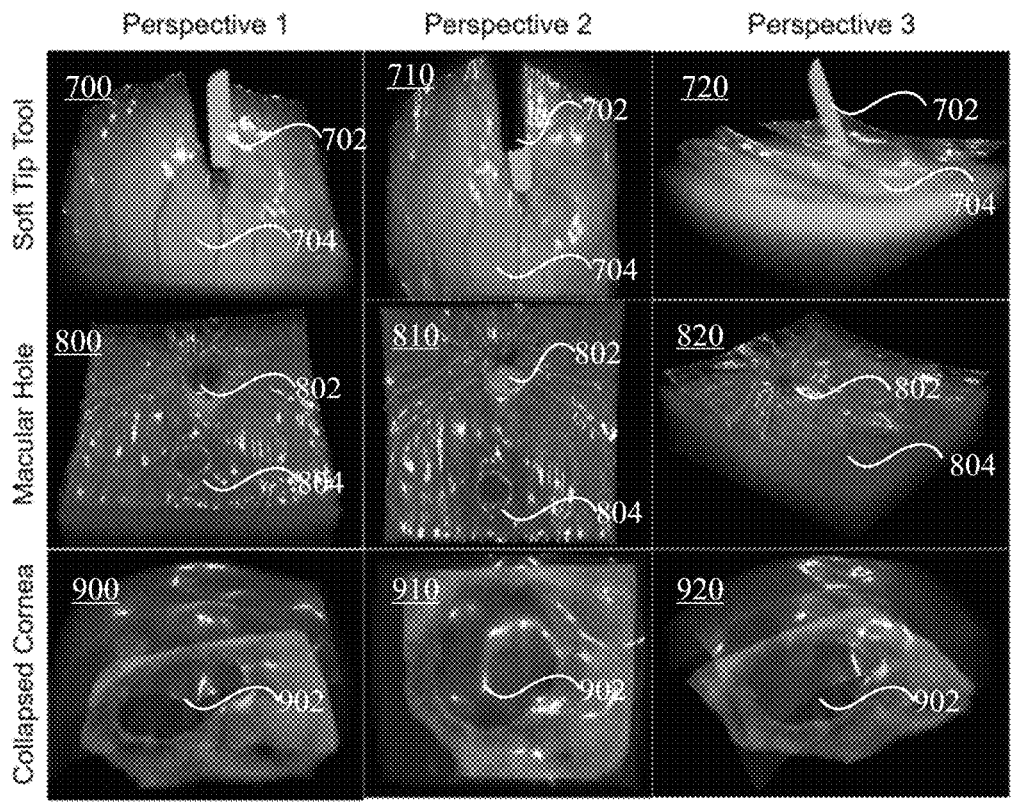
Figures 7A-7C
Figures 8A-8C
Figures 9A-9C

2D AND 3D COLOR FUSION IMAGING

CROSS-REFERENCE TO RELATED APPLICATION

This application claims the benefit of U.S. Provisional Application Ser. No. 63/186,984, filed May 11, 2021.

BACKGROUND

Eye surgery is a high-impact intervention necessary to preserve sight for thousands of patients each year. Retinal detachment surgery alone preserves sight in approximately 28,000 patients each year in the United States alone. Most standard eye surgeries are image-guided procedures where the surgeon is reliant on visualization of the region of interest through an ophthalmic microscope. Specifically, standard two-dimensional (2D) color microscopy is used to visualize the region of interest. More recently, intrasurgical optical coherence tomography (iOCT) has emerged as a supplemental imaging technique providing real-time three-dimensional (3D) visualization of the operating field. The complementary nature of these two imaging modes has led to the development and use of microscope-integrated optical coherence tomography (MIOCT) systems. These imaging platforms enable surgeons to view both the 2D and 3D image data, allowing them to integrate useful information in each modality during surgery.

While using standard 2D color microscopy images and 3D OCT images simultaneously (although separately) has improved outcomes over using only standard 2D color microscopy images, there remains room for improvement. Indeed, by having to view and process information from both standard 2D color microscopy images and 3D OCT images separately, surgeons must pay a significant cognitive overhead to mentally align images and anatomical features from the two different modalities. Thus, there is a need for improved visual presentation of the imaging data from the two different modalities to the surgeon for eye surgery as well as for surgery of other anatomy where multiple modalities are available.

BRIEF SUMMARY 2D and 3D color fusion imaging systems and methods are described herein. Advantageously, by fusing 2D color imaging data with 3D imaging data, surgeons are presented with a single image of a region of interest that includes useful information that previously required viewing separate 2D color images and 3D images and mentally aligning those images and anatomical features from the two different modalities, as well as other useful information that results from the combination of the two imaging modalities such as the reprojection of certain anatomical features that are of particular interest during surgery (e.g., vessels) and/or the ability to view the resulting image from different perspectives.

A method of fusing 2D and 3D imaging data includes receiving 3D imaging data and 2D color imaging data of a region of interest, segmenting the 3D imaging data to identify anatomical features in the region of interest, including surfaces of the anatomical features and a corresponding volume of the anatomical features, and generating an image by fusing the 2D color imaging data to the 3D imaging data according to the surfaces, the corresponding volumes, and identities of the anatomical features.

In some cases, the 3D imaging data is captured via optical coherence tomography. In some cases, the 2D color imaging data is captured via color microscopy. In some cases, segmenting the anatomical features of the region of interest using the 3D imaging data includes automatically segmenting the anatomical features of the region of interest using the 3D imaging data via one or more of image processing, machine learning, and dynamic rendering techniques. In some cases, segmenting the anatomical features of the region of interest using the 3D imaging data includes manually segmenting the anatomical features of the region of interest using the 3D imaging data. In some cases, fusing the 2D color imaging data and the 3D imaging data according to the surfaces, the corresponding volumes, and the identities of the anatomical features includes generating a cube having dimensions equal to the 3D imaging data and shading the cube according to the volume and the surface of each anatomical feature within the cube.

In some cases, the method further includes rendering a final image at an output plane by casting a ray through the fused 3D imaging data for each pixel and viewpoint of the output image plane for the image. In some cases, for each point in the fused 3D imaging data that the ray passes through, a color emission amount is integrated to a summation for that pixel and viewpoint of the output image plane for the final image. In some cases, the color emission amount for each point that the ray passes through that is integrated to the summation for that pixel and viewpoint of the output image plane for the image is based on a volume signal at that point and an average volume signal at previously integrated points. In some cases, rendering the final image at the output image plane further includes assigning a color value for that pixel and viewpoint based on the 2D color imaging data. In some cases, the method further includes creating a projection or transform of at least one anatomical feature of the anatomical features from the 3D imaging data and reprojecting a result of the projection or the transform back into the volume of the at least one anatomical feature to visualize the anatomical feature in the corresponding portion of the generated image.

In some cases, for each surface in the fused 3D imaging data that the ray intersects, a surface shader is computed from volume features at a point of surface intersection and added for that pixel and viewpoint of the output image plane for the image. In some cases, the volume features are computed as a 3D volume gradient at the point of surface intersection. In some cases, the surface shader is modulated by a surface feature orientation relative to a reference direction. In some cases, the surface shader is modulated by the surface feature orientation relative to a combination of one or more directions representing viewing directions, lighting directions, or both. In some cases, the surface shader depends on a magnitude of a horizontal component of a viewing direction. In some cases, the surface shader depends on a magnitude of a cross product of a viewing direction and a surface gradient. In some cases, the set of lighting directions contains a light directed opposite the viewing direction with a user-defined angle of pitch. In some cases, the volume features are computed as an average volume signal over a distance range above, below, or including the point of surface intersection.

One or more storage media for fusing 2D and 3D imaging data having instructions stored thereon that when executed by a processing system direct the processing system to at least receive 3D imaging data and 2D color imaging data of a region of interest, segment the 3D imaging data to identify anatomical features in the region of interest, including surfaces of the anatomical features and a corresponding volume of the anatomical features, and generate an image by fusing the 2D color imaging data to the 3D imaging data according to the surfaces, the corresponding volumes, and identities of the anatomical features.

A system for fusing 2D and 3D imaging data includes a processing system, a storage system, and instructions stored on the storage system that when executed by the processing system direct the processing system to at least receive 3D imaging data and 2D color imaging data of a region of interest, segment the 3D imaging data to identify anatomical features in the region of interest, including surfaces of the anatomical features and a corresponding volume of the anatomical features, and generate an image by fusing the 2D color imaging data to the 3D imaging data according to the surfaces, the corresponding volumes, and identities of the anatomical features.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

FIGS. 4A-4C illustrate fusion of 2D color imaging data to 3D imaging data to generate an image of a surgical tool contacting a retina.

FIGS. 5A-5C illustrate fusion of 2D color imaging data to 3D imaging data to generate an image of a macular hole in a retina.

FIGS. 6A-6C illustrate fusion of 2D color imaging data to 3D imaging data to generate an image of a collapsed cornea.

FIGS. 7A-7C illustrate images of different viewpoints of a surgical tool contacting a retina.

FIGS. 8A-8C illustrate images of different viewpoints of a macular hole in a retina.

FIGS. 9A-9C illustrate images of different viewpoints of a collapsed cornea.

DETAILED DESCRIPTION 2D and 3D color fusion imaging systems and methods are described herein. Advantageously, by fusing 2D color imaging data with 3D imaging data, surgeons are able to a single image of a region of interest that includes useful information that previously required viewing separate 2D color images and 3D images and mentally aligning those images and anatomical features from the two different modalities, as well as other useful information that results from the combination of the two imaging modalities such as the reprojection of certain anatomical features that are of particular interest during surgery (e.g., vessels) and/or the ability to view the resulting image from different perspectives.

Although examples in this specification allude to imaging of a region of interest in an eye, it should be understood that the methods and systems described herein can be applied to other areas in a body that include different anatomical features. Therefore, implementation of the systems and methods described herein can result in 3D color images of other areas in the body that include different anatomical features. Indeed, there are numerous possible applications for the disclosed systems and methods described herein, including applications that utilize 2D color imaging data and 3D imaging data to enhance visualization of a region of interest (e.g., other than an eye) during surgery, as well as non-surgical applications such as post-surgery check-ups, examinations of tissues inside a body, and post-mortem examinations of tissues inside a body. Furthermore, fusion of 2D color imaging data and 3D imaging data can be applied to many multimodal ophthalmic imaging combinations, including, but not limited to, structural 3D swept-source OCT (SSOCT), limited to time-domain OCT (TD-OCT), spectral-domain OCT (SDOCT), OCT angiography (OCT-A), color fundus 2D data, fluorescence imaging, hyperspectral imaging, scanner laser ophthalmoscopy (SLO), adaptive optics SLO (AO-SLO), confocal microscopy, polarization-sensitive-OCT (PS-OCT), spectral OCT (SOCT), and ultrasound.

Figure 1:
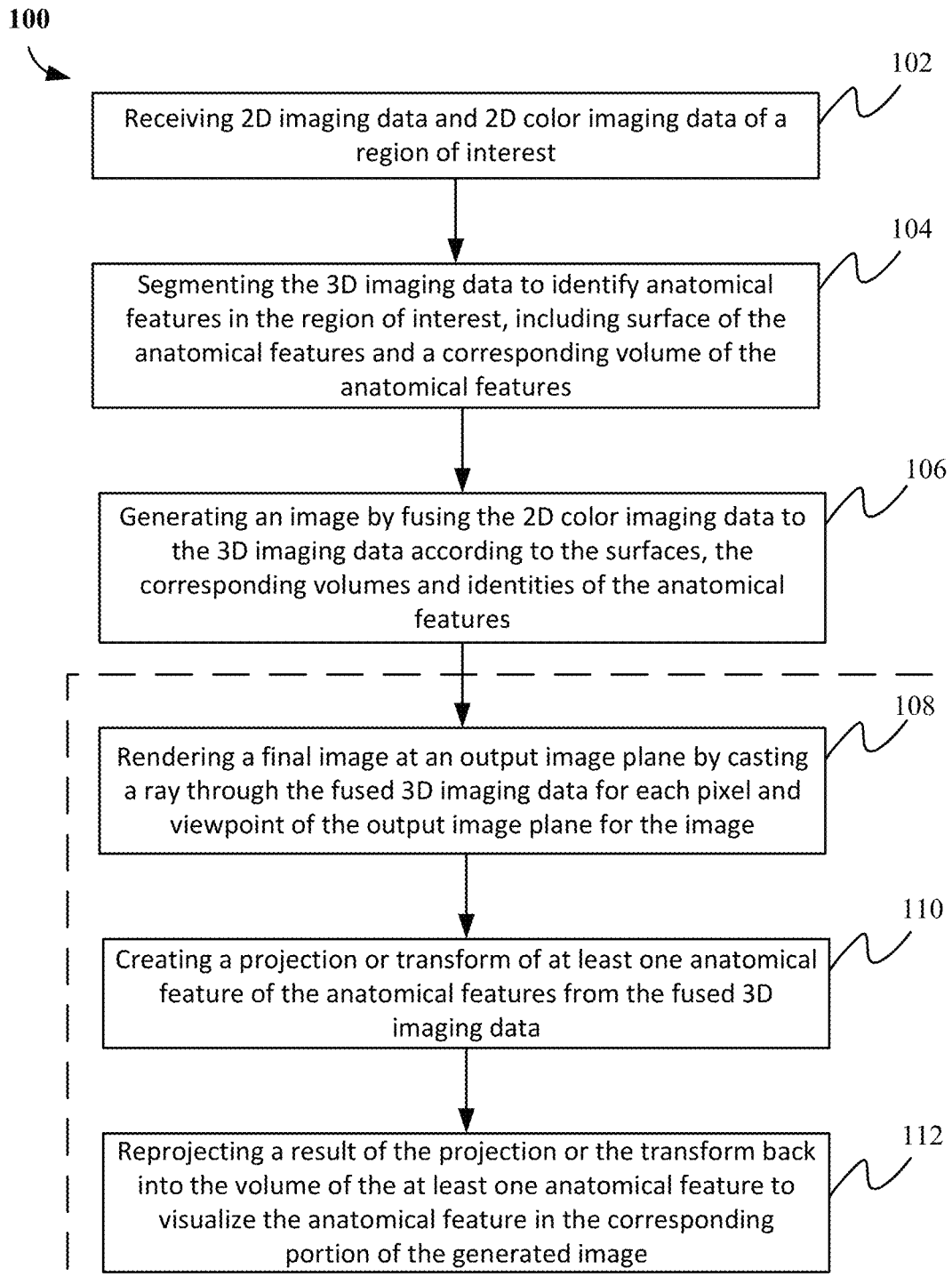
FIG. 1 illustrates a flow diagram of a method of fusing 2D and 3D imaging data to generate an image.

FIG. 1 illustrates a flow diagram of a method of fusing 2D and 3D imaging data to generate an image. In some cases, the method is performed by a 2D and 3D color fusion imaging system. Referring to FIG. 1, a method 100 of fusing 2D and 3D imaging data to generate an image includes receiving (102) 3D imaging data and 2D color imaging data of a region of interest, segmenting (104) the 3D imaging data to identify anatomical features in the region of interest, and generating (106) an image by fusing the 2D color imaging data to the 3D imaging data according to the surfaces, the corresponding volumes, and identities of the anatomical features.

In some cases, 3D imaging data is captured via a microscope optical coherence tomography (MIOCT) system and received (102) from that MIOCT system. In some cases (e.g., for real-time imaging), the MIOCT system has an imaging rate of 7 frames per second or high. In some cases, the 2D color imaging data is captured using a surgical microscopy system and received (102) from that surgical microscopy system. In some cases (e.g., for real-time imaging), the surgical microscopy system has an imaging rate of 60 frames per second. In some cases, the region of interest is an eye or a portion of the eye that includes certain anatomical features such as the retina or sub-retina. For example, a surgeon performing surgery involving the retina may wish to view real-time imaging of the retina and sub-retina during surgery. Therefore, a surgeon can use an MIOCT system to obtain the 2D and 3D imaging data needed by the 2D and 3D color fusion imaging system described herein to generate a 3D color fusion image.

Figure 2:
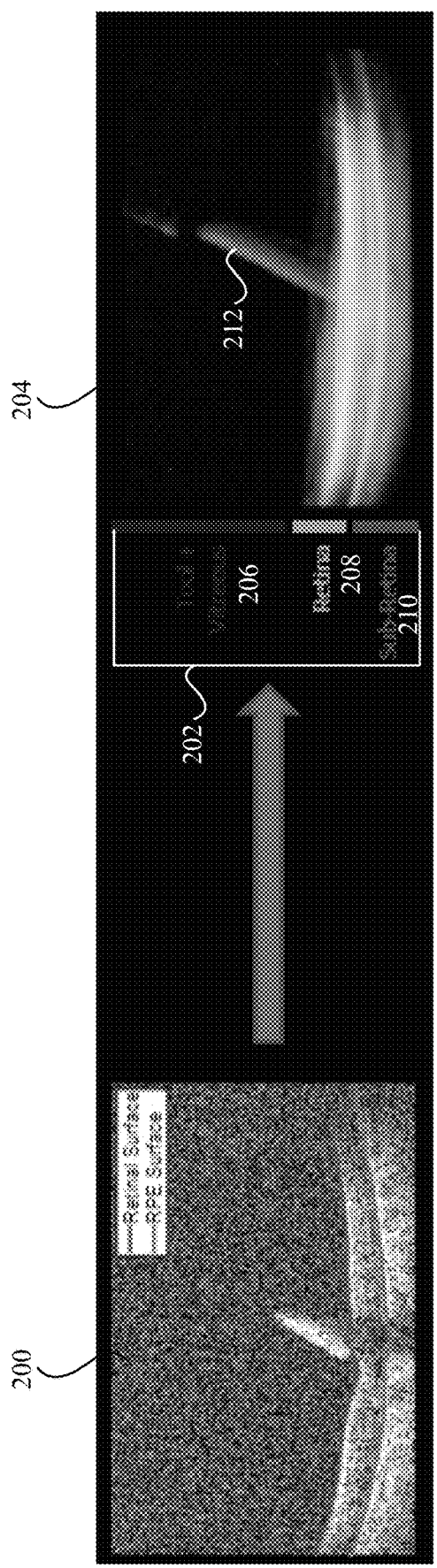
FIG. 2 illustrates an example of segmenting the 3D imaging data to identify anatomical features in the region of interest.

FIG. 2 illustrates an example of segmenting (104) the 3D imaging data to identify anatomical features in the region of interest. Referring to FIG. 2, 3D imaging data (e.g., represented as an MIOCT image 200) is segmented into volume segments 202 to identify anatomical features of a portion of an eye 204 (e.g., back of the eye), including vitreous 206 and its accompanying surface, a retina 208 and its accompanying surface, and a sub-retina 210 and its accompanying surface. A surgical tool 212 is also identified (e.g., because this is real-time 3D imaging data captured during surgery on an eye using an MIOCT system) and can be considered an anatomical feature for purposes of this invention. The surfaces of the vitreous 206, the retina 208, and the sub-retina 210 may be considered an outer portion of each of their respective volume segments. In some cases, each of these anatomical features are identified according to their intensity value in the 3D imaging data (e.g., the vitreous 206, the retina 208, and the sub-retina 210 each have their own distinct intensity value in the 3D imaging data).

In some cases, other anatomical features of an eye may be identified via segmentation, such as the cornea and iris, the optic nerve head, blood vessels, membranes, internal limiting membrane, nerve fiber layer, ganglion cell layer, inner plexiform layer, inner nuclear layer, outer plexiform layer, outer nuclear layer, external limiting membrane, Bruch's membrane, capillary choroid, choroid plexus, lens, and anterior chamber (and their accompanying surfaces).

Referring back to FIG. 1, in some cases, segmenting (104) the 3D imaging data to identify anatomical features in the region of interest includes automatically segmenting the anatomical features of the region of interest using the 3D imaging data via one or more of image processing, machine learning, and dynamic rendering techniques. In some cases (e.g., for use in situations that are not in real-time), segmenting (104) the 3D imaging data to identify anatomical features in the region of interest includes manually segmenting the anatomical features of the region of interest using the 3D imaging data.

Figure 3:
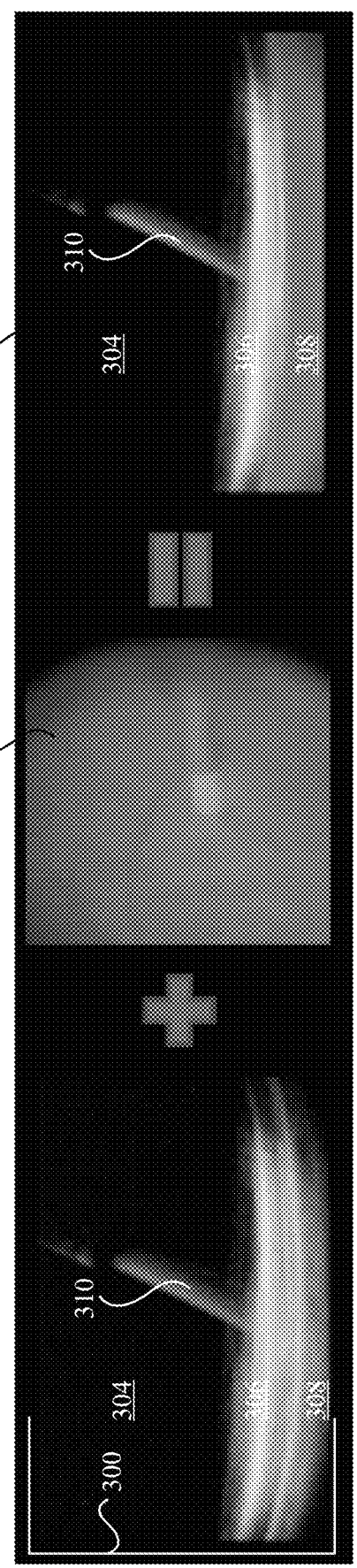
FIG. 3 illustrates an example of generating an image by fusing the 2D color imaging data to the 3D imaging data according to the surfaces, the corresponding volumes, and identities of the anatomical features.

FIG. 3 illustrates an example of generating (106) an image by fusing the 2D color imaging data to the 3D imaging data according to the surfaces, the corresponding volumes, and identities of the anatomical features. Referring to FIG. 3, the volume segments 300 of the identified anatomical features of the portion of the eye (e.g., obtained from the 3D imaging data) is fused with 2D color imaging data (e.g., represented as a surgical microscopy image 302) according to the surfaces, the corresponding volumes, and identities of the vitreous 304, the retina 306, the sub-retina 308, and the surgical tool 310 to generate (106) an image 312.

Returning back to FIG. 1, in some cases, generating (106) an image by fusing the 2D color imaging data to the 3D imaging data according to the surfaces, the corresponding volumes, and identities of the anatomical features includes generating a cube (e.g., having the anatomical features) having dimensions equal to the 3D imaging data (e.g., the region of interest and, optionally, tissue surrounding the area of interest) and shading the cube according to the volume and the surface of each anatomical feature within the cube.

FIGS. 4A-4C illustrate fusion of 2D color imaging data to 3D imaging data to generate an image of a surgical tool contacting a retina. FIGS. 5A-5C illustrate fusion of 2D color imaging data to 3D imaging data to generate an image of a macular hole in a retina. FIGS. 6A-6C illustrate fusion of 2D color imaging data to 3D imaging data to generate an image of a collapsed cornea. For example, FIGS. 4A, 5A, and 6A illustrate 3D imaging data (e.g., in the form of a 3D image 400, 500, 600) and FIGS. 4B, 5B, and 6B illustrate 2D imaging data (e.g., in the form of a 2D image 410, 510, 610). Referring to FIG. 4C, the image 420 illustrating the surgical tool 422 contacting the retina 424 is generated by fusing the 2D color imaging data (e.g., image 410) to the 3D imaging data (e.g., image 400) according to the surfaces, corresponding volumes, and identities of the anatomical features (e.g., the surgical tool 422 and the retina 424). Referring to FIG. 5C, the image 520 illustrating the macular hole 522 in the retina 524 is generated by fusing the 2D color imaging data (e.g., image 510) to the 3D imaging data (e.g., image 500) according to the surfaces, corresponding volumes, and identities of the anatomical features (e.g., the macular hole 522 and the retina 524). Referring to FIG. 6C, the image 620 illustrating the collapsed cornea 622 is generated by fusing the 2D color imaging data (e.g., image 610) to the 3D imaging data (e.g., image 600) according to the surfaces, corresponding volumes, and identities of the anatomical features (e.g., the collapsed cornea 622). It should be noted that the images 400, 410, 420, 500, 510, 520, 600, 610, and 620 also include surface shading, which is explained in more detail below. However, in some cases, surface shading is not required to generate the image.

Returning back to FIG. 1, in some cases, the method 100 further includes rendering (108) a final image at an output image plane by casting a ray through the fused 3D imaging data for each pixel and viewpoint of the output image plane for the image. FIGS. 7A-7C illustrate images of different viewpoints of a surgical tool contacting a retina. FIGS. 8A-8C illustrate images of different viewpoints of a macular hole in a retina. FIGS. 9A-9C illustrate images of different viewpoints of a collapsed cornea. Referring to FIGS. 7A-9C, a ray is cast for each pixel and the viewpoint through the fused 3D imaging data. For example, FIGS. 7A, 8A, and 9A illustrate a side-angled viewpoint of the anatomical features in their respective image (e.g., FIG. 7A illustrates a final image 700 of a surgical tool 702 contacting a retina 704; FIG. 8A illustrates a final image 800 of a macular hole 802 in a retina 804; FIG. 9A illustrates a final image 900 of a collapsed cornea 902), FIGS. 7B, 8B, and 9B illustrate top-down views of the anatomical features in their respective image (e.g., FIG. 7B illustrates a final image 710 of the surgical tool 702 contacting the retina 704; FIG. 8B illustrates a final image 810 of the macular hole 802 in the retina 804; FIG. 9B illustrates a final image 910 of the collapsed cornea 902), and FIGS. 7C, 8C, and 9C illustrate corner-angled views of the anatomical features in their respective image (e.g., FIG. 7C illustrates a final image 720 of the surgical tool 702 contacting the retina 704; FIG. 8C illustrates a final image 820 of the macular hole 802 in the retina 804; FIG. 9C illustrates a final image 920 of the collapsed cornea 902). Therefore, as applied to FIGS. 7A-9C, these final images are rendered at the output plane (e.g., the plane of the final images) by casting a ray through the fused 3D image data for each pixel (e.g., the pixels in the final images 700, 710, 720, 800, 810, 820, 900, 910, and 920) and viewpoint (e.g., side-angled, top-down, and/or corner-angled) of the output image plane for the image. It should be noted that the final images 700, 710, 720, 800, 810, 820, 900, 910, and 920 also include surface shading, which is explained in more detail below. However, in some cases, surface shading is not required to render the final image.

Figure 10:
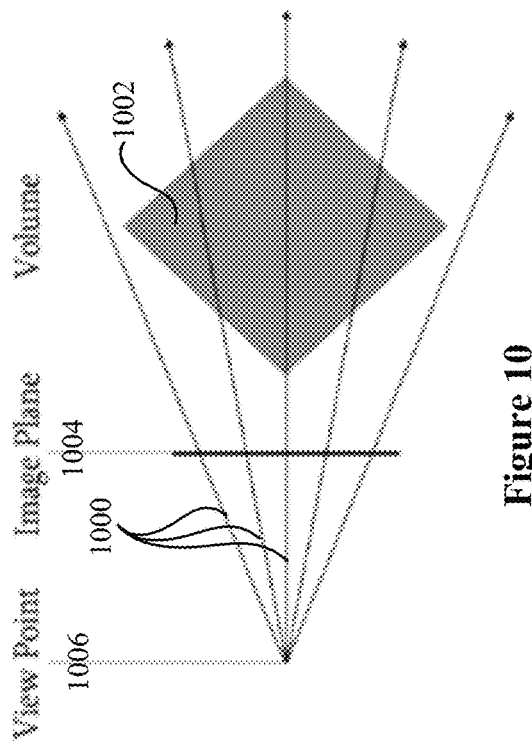
FIG. 10 illustrates a conceptual view of casting a ray through the fused 3D imaging data for each pixel and viewpoint of the output image plane for the image.

FIG. 10 illustrates a conceptual view of casting a ray through the fused 3D imaging data for each pixel and viewpoint of the output image plane for the image. Referring to FIG. 10, a ray 1000 is cast through the fused 3D imaging data 1002 for each pixel (e.g., a ray 1000 is cast for each pixel of an output image plane 1004) and viewpoint 1006 (e.g., the viewpoint is the same for each ray 1000 that is cast through the fused 3D data) of the output image plane 1004 for the image. An expression for the value of the corresponding pixel at a given position (e.g., x, y) in the output image plane 1004 given emission (ε) and density (α) over positions $r_n$ along the ray is as follows:

$$I(x,y)=\Sigma_{i=0}^{M-1}\varepsilon(r_i)\Pi_{k=0}^{i}(1-\alpha(r_k))$$

For each pixel in the output image plane 1004, a ray 1000 intersecting the pixel and viewpoint 1006 is cast through the 3D imaging data 1002, integrating an amount of emission (ε) for each point in the 3D imaging data 1002 the ray 1000 passes through; this amount depends on the density (α) at the point and the density at previously integrating points, attenuating the contribution of the current emission value in a manner analogous to Beer's Law. Once the emission contribution of a sample on the ray 1000 falls below a predetermined threshold value (e.g., predetermined based on the values that are associated with the identity of the anatomical feature(s) that are expected for that volume), or the ray 1000 exits the data volume, the ray 1000 terminates and colors its associated pixel with the emission it has integrated up to that point.

In some cases, for each point in the fused 3D imaging data 1002 that the ray 1000 passes through, a color emission amount is integrated to a summation for that pixel and viewpoint 1006 of the output image plane 1004 for the final image. In some cases, the color emission amount for each point that the ray 1000 passes through that is integrated to the summation for that pixel and viewpoint 1006 of the output image plane 1004 for the image is based on a volume signal at that point and an average volume signal at previously integrated points. In some cases, rendering the final image at the output image plane 1004 further includes assigning a color value for that pixel and viewpoint 1006 based on the 2D color imaging data.

In order to visualize the detected surface, there are many methods of surface shading available. For this application, the goal is to provide the viewer (e.g., the surgeon) with the best possible perception of the shape and location of surfaces while maintaining visibility of features that lie behind the surface (e.g., color and other anatomical features). These two goals require balancing to achieve the best possible image for the viewer.

In some cases, for each surface in the fused 3D imaging data 1002 that the ray 1000 intersects, a surface shader is computed from volume features at a point of surface intersection and added for that pixel and viewpoint 1006 of the output image plan 1004 for the image. In some cases, the volume features are computed as a 3D volume gradient at the point of surface intersection. In some cases, the volume features are computed as an average volume signal over a distance below the point of surface intersection. In some cases, the surface shader is modulated by a surface feature orientation relative to a reference direction. In some cases, the surface shader is modulated by the surface feature orientation relative to a combination of one or more directions representing viewing directions, lighting directions, or both. In some cases, a set of lighting directions is selected to optimize visualization of the surfaces. For example, the set of lighting directions may include an overhead light directed downwards towards the surfaces. The set of lighting directions may additionally or alternatively include a light directed coaxial with the viewing direction. In some cases, the set of lighting directions includes a light directed opposite the viewing direction, with a user-defined (and/or predetermined) angle of pitch. In some cases, the surface shader depends on a magnitude of a horizontal component of a viewing direction. In some cases, the surface shader depends on a magnitude of a cross product of a viewing direction and a surface gradient.

In some cases, a specular surface shader is used to produce shades for the surface that are generally a function of the surface normal direction (e.g., direction that is perpendicular to the surface), lighting direction, and viewing direction. In some cases, computation of a specular surface shader includes summing a viewing vector and a lighting vector, finding the dot product of the surface normal and the sum of the viewing vector and the lighting vector, finding the absolute value of the dot product of the surface normal and the sum of the viewing vector and the lighting vector, and raising the result to the power of the sharpness factor. If the result is greater than 1, then the value should be set to 1 (e.g., "clamping" to 1). The specular surface shader then sets the red, green, blue, and opacity values equal to the result (e.g., for RGB-based coloration).

Reflectance 'sharpness' qualitatively refers to how shiny (e.g., sharp) or matte (e.g., soft) a reflection appears from a surface. For the purposes of communicating surface details, sharp reflections are more effective at illustrating subtle changes to local surface orientation, but are not very effective at illustrating surface orientations that differ greatly. In other words, sharp reflections provide high resolution but low dynamic range when visualizing surface orientation. On the other hand, soft reflections are more effective at illustrating surface orientations that differ greatly, but are not very effective at illustrating subtle changes to local surface orientation. In other words, soft reflections provide low resolution but high dynamic range when visualizing surface orientation.

Figure 12:
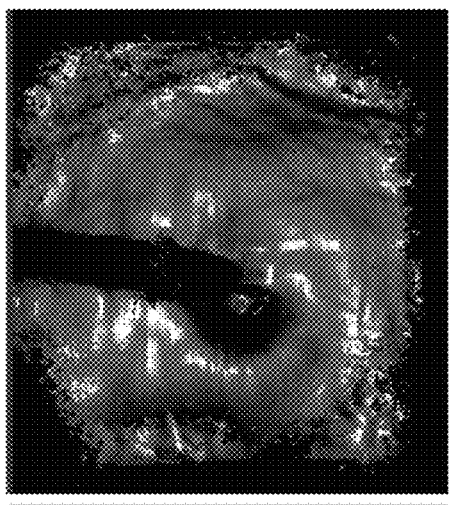
FIG. 12 illustrates a coaxial illumination, soft specular surface shader.
Figure 11:
FIG. 11 illustrates a coaxial illumination, sharp specular surface shader.

Four specific examples of a specular surface shader include 1) coaxial illumination, sharp, 2) coaxial illumination, soft, 3) opposing illumination, sharp, and 4) opposing illumination, soft. These examples may be used together to form a set of lighting directions. The coaxial illumination, sharp specular surface shader includes modeling sharp (e.g., sharp factor ~2000) reflectance to the viewer from a light source pointed in the same direction as the viewing direction. Weight of 1 is used for this shader. FIG. 11 illustrates a coaxial illumination, sharp specular surface shader. The coaxial illumination, soft specular surface shader includes modeling soft (e.g., sharp factor ~50) reflectance to the viewer from a light source pointed in the same direction as the viewing direction. Weight of 0.5 is used for this shader. FIG. 12 illustrates a coaxial illumination, soft specular surface shader. The opposing illumination, sharp specular surface shader includes modeling sharp (e.g., sharp factor ~2000) reflectance to the viewer from a light source pointed opposite the viewer at a user-defined or predetermined pitch (e.g., 45 degrees downward). Weight of 0.5 is used for this shader. The opposing illumination, soft specular shader includes modeling soft (e.g., sharp factor ~50) reflectance to the viewer from a light source pointed in opposite the viewer at a user-defined or predetermined pitch (e.g., 45 degrees downward). Weight of 0.5 is used for this shader.

In any case, the directions of the set of lighting directions are selected to provide the most informative and intuitive visualization of the surface. Referring to the set of lighting directions provided above, the coaxial lighting direction provides specular highlights to surfaces when a surface is perpendicular to the viewer, while the opposing lighting direction provides specular highlights to surfaces when a surface is tilted away from the viewer by the pitch angle of the light source. In various implementations, the selection of the lighting directions can be based on qualitative feedback from the viewers (e.g., surgeons) who determine which set of lights and their parameters provide the most intuitive presentation of the surface(s) for the application (e.g., eye surgery).

In some cases, a Lambertian/diffuse surface shader is used to produce shades for the surface that are generally dependent on lighting and surface normal directions, but are independent of the viewing direction. In some cases, computation of a Lambertian/diffuse surface shader includes finding the dot product of the surface normal and the lighting vector, finding the absolute value of the dot product of the surface normal and the lighting vector, and raising the result to the power of the sharpness factor. If the result is greater than 1, then the value should be set to 1 (e.g., "clamping" to 1). The Lambertian/diffuse surface shader then sets the red, green, blue, and opacity values equal to the result.

In some cases, an ambient surface shader is used to produce shades for the surface that are generally independent of all directional conditions. However, there is no computation for an ambient surface shader as the values are set to constants. Additional potential embodiments exist which apply different illumination and/or different shaders to the surface to enhance or suppress other features including but not limited to ambient occlusion, scene reflection, and curvature-based shading.

In some cases, volume data (e.g., the fused 3D imaging data) is sampled via linear interpolation at a series of steps in distance in order along the ray direction. As the samples are acquired, each of the samples are input to a pair of transfer functions whose parameters depend on the objective of the visualization and nature of the volume data. The transfer functions reach a threshold and convert the samples to a new value. One of the transfer functions (e.g., the surface shader) computes values for shading (e.g., color), while the other transfer function (e.g., a mass transfer function) computes mass and size in the region of interest to identify anatomical features.

A specific embodiment of a mass transfer function receives 3D imaging data and generates a cube (e.g., having the anatomical features) having dimensions equal to the 3D imaging data (e.g., the region of interest and, optionally, tissue surrounding the area of interest). In some cases, the 3D imaging data may include a density value for each point in space of the cube that ranges from 0 to 255 (e.g., 8-bit range). The mass transfer function then shifts the density values down by 50 (e.g., a 0 density value becomes −50 and a 255 density value becomes 205). The mass transfer function then sets all negative values to 0 (e.g., "thresholding") to prevent noise (e.g., density values that were originally from a 0 to 50 range that are assumed to be noise) from taking up dynamic range in the image.

The mass transfer function then multiplies the resulting data by a factor that converts the 0 to 205 range of density values to a 0 to 1 range of density values (e.g., "rescaling"). This rescaling can serve multiple purposes. In some cases, rescaling is used to normalize the range of values for comparison with those of another transfer function (e.g., a mass shader) with different parameters (e.g., different threshold values). In some cases, the rescaling is used to implement the shader because the shader values must range from 0 to 1 in most graphics implementations.

Thus, the mass transfer function can be a sigmoid of a specific shift and scale. After rescaling, the anatomical features may be identified based on their density values and the surfaces and volumes (e.g., shapes) those values form and the cube can be shaded according to the volume and the surface of each anatomical feature within the cube, with input from the 2D color imaging data. Specifically, the result of the mass transfer function is used to determine if a surface has been intercepted by the ray by determining if/when the accumulated mass increases beyond a threshold, at which that point on the ray where the accumulated mass increased beyond a threshold is identified as the point where the ray intersected a surface. In this way, the intersections found by all the rays (for each pixel in the image) account for all of the surfaces in the image. In any case, at the point of intersection of the ray with the surface, the surface normal at that point is approximated as the 3D gradient vector at that point.

It should be understood that the above specific embodiment is merely illustrative of a transfer function that can be used. The above specific embodiment of the mass transfer function only includes parameters that include the value of the threshold (e.g., 50) and the rescale factor (e.g., 1/205), but a similar approach can be applied to any function that takes some set of data (whether a single sample or the entire dataset at once) and produces an output of a single value or more values (e.g., even more than the number of samples included in the 3D imaging data).

A specific embodiment of a shader function includes summing the values (e.g., emission and/or density) as they are computed during the stepping of the ray (e.g., as the ray moves through the 3D imaging data). The result of the shader function is a shade that includes a set of four values (e.g., with each value being between 0 and 1) for generating a color. Each value of the set of four values is for one of red, green, blue, and opacity. The opacity dictates how the shader is combined with other shaders (e.g., lighting directions and their reflection on the surfaces in the final image). In most standard graphics implementations, opacity serves as the weight for each shader, and their opacity-weighted sum is computed to combine them.

In some cases, following the computation of the surface shader, an argmax surface (the surface that gives the maximum value from a target function) is determined as a surface to project color onto for the output image plane. The argmax surface is determined by finding a position of the maximum value for each vertical column in the cube/3D imaging data. The position of the maximum value from each vertical column in the cube/3D imaging data forms the argmax surface. An argmax surface is useful for differentiating between anatomical features. For example, the majority of a retina is composed of retinal pigmented epithelium (RPE) and retinal blood vessels, which are responsible for the majority of coloration. Therefore, an argmax surface can be used to clearly illustrate different anatomical features (e.g., including a clearly defined surgical tool). Through subsurface averaging and multiplication (e.g., as explained below with respect to FIGS. 13A-13C), a more intuitive illustration of subsurface features can be achieved by multiplying the intensity of the shading of the subsurface features with the color image.

Figure 13C:
FIGS. 13A-13C illustrate an image of a surgical tool contacting a retina.
Figure 13B:
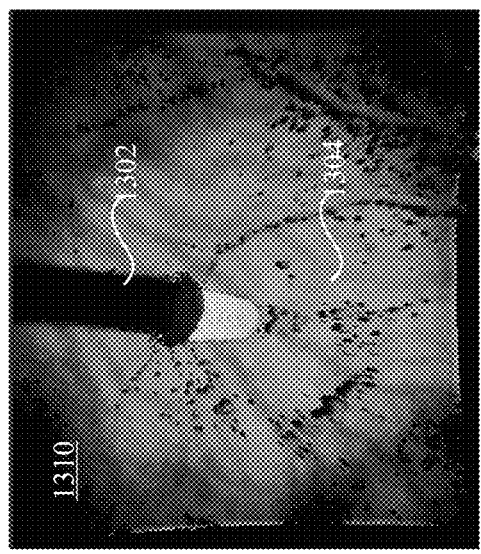
Figure 13A:
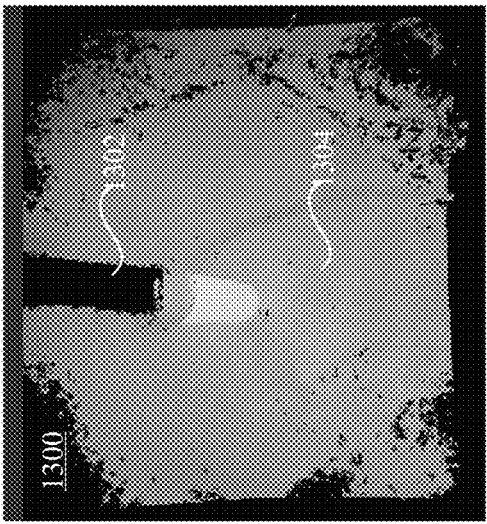

FIGS. 13A-13C illustrate an image of a surgical tool contacting a retina. Referring to FIG. 13A, an image 1300 of a surgical tool 1302 contacting a retina 1304 is generated by advancing the ray from the previous surface intersection point until the ray is below the argmax surface and sampling the color from the corresponding position in the 2D color imaging data/color image. Referring to FIG. 13B, an image 1310 of the surgical tool 1302 contacting the retina 1304 is generated by calculating an average value from the 3D imaging data/cube at a fixed distance below the argmax surface, passing that average value through a transfer function (e.g., mass transfer function), and multiplying the color values by the result of passing that average value through the transfer function. Referring to FIG. 13C, a final image 1320 of the surgical tool 1302 contacting the retina 1304 is generated by weighting the color shading from FIG. 13B and adding that result to a set of lighting directions that was previously generated.

Returning back to FIG. 1, in some cases, the method 100 further includes creating (110) a projection or transform of at least one anatomical feature of the anatomical features from the 3D imaging data and reprojecting (112) a result of the projection or the transform back into the volume of the at least one anatomical feature to visualize the anatomical feature in the corresponding portion of the generated image.

Figure 14:
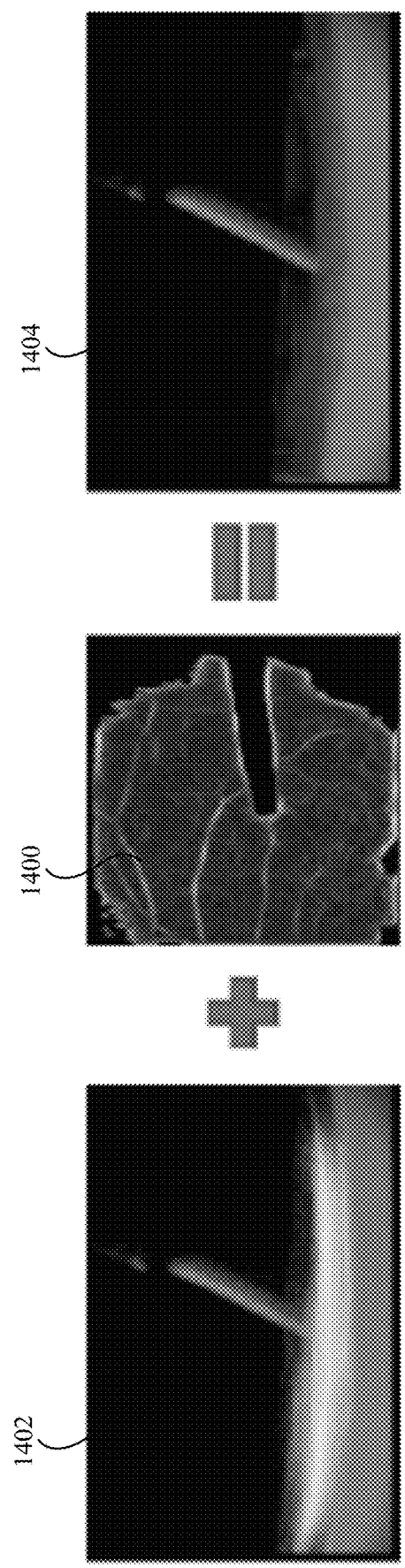
FIG. 14 illustrates an example of reprojecting a result of a projection or a transform back into a volume of at least one anatomical feature in a generated image.

FIG. 14 illustrates an example of reprojecting (112) a result of a projection or a transform back into a volume of at least one anatomical feature in a generated image. Referring to FIG. 10, a projection or a transform of vessels 1400 is created (110) from the 3D imaging data and a result of the projection or transform of the vessels 1400 is reprojected (112) back into the volume of the vessels (e.g., of the generated image 1402/image 312 of FIG. 3) to visualize the vessels in the corresponding portion of the generated image 1404. In some cases in which a surface shader is also used, reprojecting the result of the projection or transform back into the volume of the at least one anatomical feature in the generated image may occur before or after the surface shader is applied to the generated image.

Figure 15:
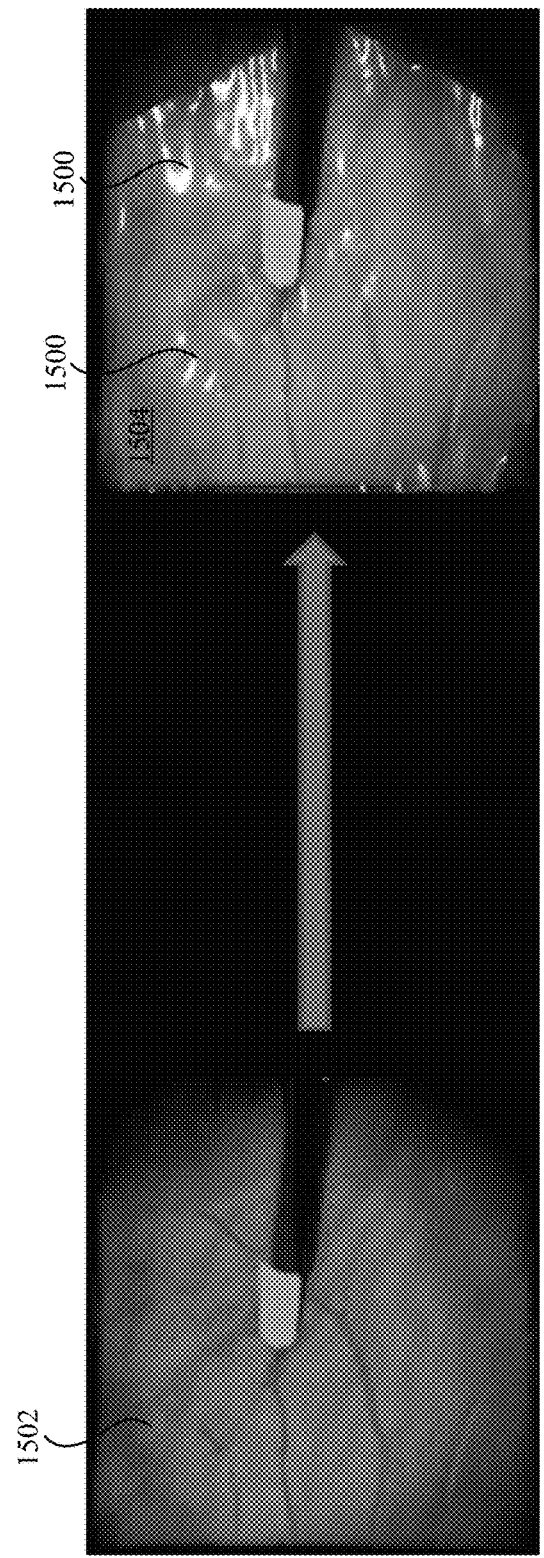
FIG. 15 illustrates an example of a set of lighting directions being applied to the generated image of FIG. 14 via a surface shader.

FIG. 15 illustrates an example of a set of lighting directions being applied to the generated image 1404 of FIG. 14 via a surface shader. Referring to FIG. 15, hard and soft reflections 1500 are applied to the generated image 1502 (e.g., a different perspective/viewpoint of generated image 1404 of FIG. 14) to generate a final image 1504 via one or more methods described above with respect to surface shading.

Figure 16:
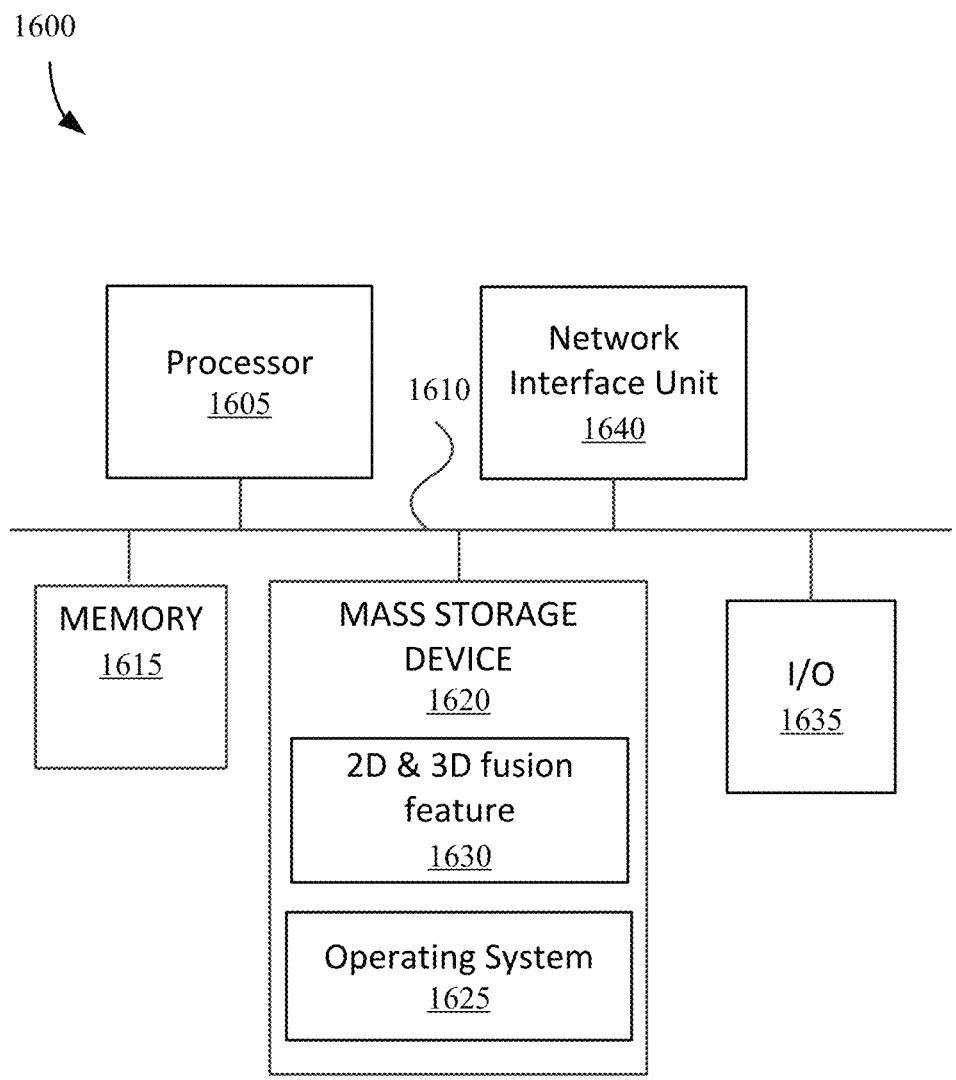
FIG. 16 illustrates a block diagram illustrating components of a computing device used in some embodiments.

FIG. 16 illustrates a block diagram illustrating components of a computing device used in some embodiments. It should be understood that aspects of the system described herein are applicable to both mobile and traditional desktop computers, as well as server computers and other computer systems. Components of computing device 1600 may represent an imaging system, a personal computer, a reader, a mobile device, a personal digital assistant, a wearable computer, a smart phone, a tablet, a laptop computer (notebook or netbook), a gaming device or console, an entertainment device, a hybrid computer, a desktop computer, a smart television, or an electronic whiteboard or large form-factor touchscreen as some examples. Accordingly, more or fewer elements described with respect to computing device 1600 may be incorporated to implement a particular computing device.

Referring to FIG. 16, a computing device 1600 can include at least one processor 1605 connected to components via a system bus 1610; a system memory 1615 and a mass storage device 1620. A processor 1605 processes data according to an operating system 1625. Examples of processor 1605 include general purpose central processing units (CPUs), graphics processing units (GPUs), field programmable gate arrays (FPGAs), application specific processors, and logic devices, as well as any other type of processing device, combinations, or variations thereof.

It can be understood that the mass storage device 1620 may involve one or more memory components including integrated and removable memory components and that one or more of the memory components can store the operating system 1625. Mass storage device 1620 further stores the instructions for the 2D & 3D fusion feature 1630; and can store image data (not shown) used by the feature 1630. Examples of mass storage device 1620 include removable and non-removable storage media including random access memory, read only memory, magnetic disks, optical disks, CDs, DVDs, flash memory, magnetic cassettes, magnetic tape, magnetic disk storage or other magnetic storage devices, or any other suitable storage media. Mass storage device 1620 does not consist of propagating signals or carrier waves.

The system memory 1615 may include a random-access memory ("RAM") and/or a read-only memory ("ROM"). The RAM generally provides a local storage and/or cache during processor operations and the ROM generally stores the basic routines that help to transfer information between elements within the computer architecture such as during startup.

2D & 3D fusion feature 1630 includes the instructions for performing the processes described herein (e.g., method 100 and various implementations described above).

The system can further include user interface system 1635, which may include input/output (I/O) devices and components that enable communication between a user and the computing device 1600. User interface system 1635 can include one or more input devices such as, but not limited to, a mouse, track pad, keyboard, a touch device for receiving a touch gesture from a user, a motion input device for detecting non-touch gestures and other motions by a user, a microphone for detecting speech, and other types of input devices and their associated processing elements capable of receiving user input.

The user interface system 1635 may also include one or more output devices such as, but not limited to, display screen(s), speakers, haptic devices for tactile feedback, and other types of output devices. In certain cases, the input and output devices may be combined in a single device, such as a touchscreen display which both depicts images and receives touch gesture input from the user.

The network interface 1640 allows the system to communicate with other computing devices, including server computing devices and other client devices, over a network. The network interface 1640 can include a unit to perform the function of transmitting and receiving radio frequency communications to facilitate wireless connectivity between the system and the "outside world," via a communications carrier or service provider In various implementations, data/information stored via the system may include data caches stored locally on the device or the data may be stored on any number of storage media that may be accessed by the device via the network interface 1640 or via a wired connection between the device and a separate computing device associated with the device, for example, a server computer in a distributed computing network, such as the Internet. As should be appreciated such data/information may be accessed through the device via the network interface 1640 or a distributed computing network. Similarly, such data/information may be readily transferred between computing devices for storage and use according to well-known data/information transfer and storage means, including electronic mail and collaborative data/information sharing systems.

Certain techniques set forth herein may be described in the general context of computer-executable instructions, such as program modules, executed by one or more computing devices. Generally, program modules include routines, programs, objects, components, and data structures that perform particular tasks or implement particular abstract data types.

Embodiments may be implemented as a computer process, a computing system, or as an article of manufacture, such as a computer program product or computer-readable medium. Certain methods and processes described herein can be embodied as code and/or data, which may be stored on one or more computer-readable media. Certain embodiments of the invention contemplate the use of a machine in the form of a computer system within which a set of instructions, when executed, can cause the system to perform any one or more of the methodologies discussed above. Certain computer program products may be one or more computer-readable storage media readable by a computer system and encoding a computer program of instructions for executing a computer process.

It should be understood that as used herein, in no case do the terms "storage media," "computer-readable storage media" or "computer-readable storage medium" consist of transitory carrier waves or propagating signals. Instead, "storage" media refers to non-transitory media.

The functional block diagrams, operational scenarios and sequences, and flow diagrams provided in the Figures are representative of exemplary systems, environments, and methodologies for performing novel aspects of the disclosure. While, for purposes of simplicity of explanation, methods included herein may be in the form of a functional diagram, operational scenario or sequence, or flow diagram, and may be described as a series of acts, it is to be understood and appreciated that the methods are not limited by the order of acts, as some acts may, in accordance therewith, occur in a different order and/or concurrently with other acts from that shown and described herein. For example, those skilled in the art will understand and appreciate that a method could alternatively be represented as a series of interrelated states or events, such as in a state diagram. Moreover, not all acts illustrated in a methodology may be required for a novel implementation.

Experiment

The inventors conducted an experiment following an implementation similar to those described with respect to FIGS. 2, 3, 14, and 15. For MIOCT image data acquisition, the inventors used a system including a commercially available Enfocus MIOCT scanner modified for high speed swept source OCT. The OCT engine utilized a 400 kHz, 1050 nm swept frequency laser that is introduced into the modified scanner, illuminating a transmissive Mach-Zender interferometer. A Truevision (Goleta, CA) 3D visualization system was used to provide heads up, stereoscopic visualization of both the surgical field and OCT data on a 3D TV. Image data from both the camera and OCT engine was processed and recorded by an on-board computer running custom-built acquisition and processing software.

Fusion of the acquired eye imaging data began with manual segmentation into anatomical features of interest. Specifically, the b-scans (e.g., slices) of each volume were imported to MATLAB and manually segmented by hand using Duke OCT Retinal Analysis Program (DOCTRAP; Duke University, Durham, NC, USA). Following this, the corresponding color microscopy image was manually registered to the MIP of the volume data in MATLAB using the cpselect( ) and imwarp( ) functions.

Volume segments were converted to native volume data format (.vdb) of the open source 3D rendering program Blender via functions available in the Open VDB python library. After importing the volume and color data to Blender, a cube of dimensions equal to the OCT data was generated and shaded using a principled volume shader to volumetrically shade based on the image data. The result was then rendered via direct volume rendering (DVR) implemented by ray casting (e.g., as explained above) with front-to-back over-operator composition.

Emission and density were computed in different ways depending on the identity of the volume segment. The sub-iris and non-retinal volumes emissions (corresponding to the volume data of the iris and choroid below the retina, respectively) were colored with microscopy image data. To do so, their emission was computed as proportional to the product of the OCT intensity with the RGB value of the axial projection of the registered microscopy image, while their densities were computed proportional to the OCT intensity (see FIG. 3 for rear of eye retina example). The corneal volume, while transparent in reality, was assigned a constant-valued emission and density to slightly cloud the volume for better perception of its extent in space.

Additionally, in the retinal case, axial maximum-intensity projection (MIP) of the volume within +/−20 um of the RPE surface was computed within MATLAB to obtain a high-contrast projection of the retinal vessel shadows. After suppressing non-vessel features (optic nerve head) via regionfill( ), vessels in the result were further enhanced via a filter bank consisting of a line template oriented in 30 directions evenly spaced between 0 and 180 degrees. Taking the maximum response over these filter orientations yielded a vessel-enhanced image. The retinal volume emission was computed as the product of the OCT intensity, the axial projection of the imported enhanced vessel image, and a predetermined RGB color value to pseudo color the vessels with a bloody hue (see FIG. 14). Volume density was computed in the same fashion (with the exception of the pseudo coloring).

Finally, images of the height maps of the segmented surfaces were generated in MATLAB and imported to Blender. For each surface to be rendered (e.g., retinal surface, front corneal surface, back corneal surface), a flat plane was generated of a size equal to the lateral dimensions of the volume cube. A displacement modifier was then added to the plane with the displacement magnitude driven by the imported height map of the surface. After trimming surface artifacts from shadowing and vignetting, the resulting high-density surface mesh was smoothed and shaded with a composition of two specular (reflective) Phong shaders. The first shader is a hard specular shader (hardness 0.95) weighted at 95%, with the remaining 5% consisting of a softer specular shader (hardness 0.4). The rendered result communicates a combination of fine surface detail from the sharpness of the hard reflections, along with some context of the surface surrounding the hard highlights provided by the broader soft reflections (see FIG. 15). Illumination for surfaces was modeled with six distant (sun) light sources, four statically positioned on each side of the volume pointed −45 degrees from horizontal, and two dynamic distant light sources, one tracked to the viewing direction, and the other tracked to the reflection angle of the viewing direction off the horizontal plane.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

Although the subject matter has been described in language specific to structural features and/or acts, it is to be understood that the subject matter defined in the appended claims is not necessarily limited to the specific features or acts described above. Rather, the specific features and acts described above are disclosed as examples of implementing the claims and other equivalent features and acts are intended to be within the scope of the claims.

What is claimed is:

1. A method comprising:
   receiving 3D imaging data and 2D color imaging data of a region of interest;
   segmenting the 3D imaging data to identify anatomical features in the region of interest, including surfaces of the anatomical features and a corresponding volume of the anatomical features;
   generating an image by fusing the 2D color imaging data to the 3D imaging data according to the surfaces, the corresponding volumes, and identities of the anatomical features; and
   rendering a final image at an output image plane by casting a ray through a fused 3D imaging data of the image generated by fusing the 2D color imaging data to the 3D imaging data for each pixel and viewpoint of the output image plane for the image,
   wherein for each surface in the fused 3D imaging data that the ray intersects, a surface shader is computed from volume features at a point of surface intersection and added for that pixel and viewpoint of the output image plane for the image.

2. The method of claim 1, wherein the 3D imaging data is captured via optical coherence tomography.

3. The method of claim 1, wherein the 2D color imaging data is captured via color microscopy.

4. The method of claim 1, wherein segmenting the anatomical features of the region of interest using the 3D imaging data comprises automatically segmenting the anatomical features of the region of interest using the 3D imaging data via one or more of image processing, machine learning, and dynamic rendering techniques.

5. The method of claim 1, wherein fusing the 2D color imaging data and the 3D imaging data according to the surfaces, the corresponding volumes, and the identities of the anatomical features comprise:
   generating a cube having dimensions equal to the 3D imaging data; and
   shading the cube according to the corresponding volume and the surface of each anatomical feature within the cube.

6. The method of claim 1, wherein for each point in the fused 3D imaging data that the ray passes through, a color emission amount is integrated to a summation for that pixel and viewpoint of the output image plane for the final image.

7. The method of claim 6, wherein the color emission amount for each point that the ray passes through that is integrated to the summation for that pixel and viewpoint of the output image plane for the image is based on a volume signal at that point and an average volume signal at previously integrated points.

8. The method of claim 1, wherein the volume features are computed as a 3D volume gradient at the point of surface intersection.

9. The method of claim 1, wherein the surface shader is modulated by a surface feature orientation relative to a reference direction.

10. The method of claim 9, wherein the surface shader is modulated by the surface feature orientation relative to a combination of one or more directions representing viewing directions, lighting directions, or both.

11. The method of claim 10, wherein the surface shader depends on a magnitude of a horizontal component of a viewing direction.

12. The method of claim 10, wherein the surface shader depends on a magnitude of a cross product of a viewing direction and a surface gradient.

13. The method of claim 10, wherein a set of lighting directions comprises a light directed opposite the viewing direction with a user-defined angle of pitch.

14. The method of claim 1, wherein the volume features are computed as an average volume signal over a distance below the point of surface intersection.

15. The method of claim 1, wherein rendering the final image at the output image plane further comprises assigning a color value for that pixel and viewpoint based on the 2D color imaging data.

16. The method of claim 1, further comprising:
   creating a projection or transform of at least one anatomical feature of the anatomical features from a fused 3D imaging data of the image generated by fusing the 2D color imaging data to the 3D imaging data; and
   reprojecting a result of the projection or the transform back into the volume of the at least one anatomical feature to visualize the anatomical feature in a corresponding portion of the generated image.

17. One or more storage media having instructions stored thereon that when executed by a processing system direct the processing system to at least:
   receive 3D imaging data and 2D color imaging data of a region of interest;
   segment the 3D imaging data to identify anatomical features in the region of interest, including surfaces of the anatomical features and a corresponding volume of the anatomical features;
   generate an image by fusing the 2D color imaging data to the 3D imaging data according to the surfaces, the corresponding volumes, and identities of the anatomical features; and
   render a final image at an output image plane by casting a ray through a fused 3D imaging data of the image generated by fusing the 2D color imaging data to the 3D imaging data for each pixel and viewpoint of the output image plane for the image,
   wherein for each surface in the fused 3D imaging data that the ray intersects, a surface shader is computed from volume features at a point of surface intersection and added for that pixel and viewpoint of the output image plane for the image.

18. A system comprising:
a processing system;
a storage system; and
instructions stored on the storage system that when executed by the processing system direct the processing system to at least:
receive 3D imaging data and 2D color imaging data of a region of interest;
segment the 3D imaging data to identify anatomical features in the region of interest, including surfaces of the anatomical features and a corresponding volume of the anatomical features;
generate an image by fusing the 2D color imaging data to the 3D imaging data according to the surfaces, the corresponding volumes, and identities of the anatomical features; and
render a final image at an output image plane by casting a ray through a fused 3D imaging data of the image generated by fusing the 2D color imaging data to the 3D imaging data for each pixel and viewpoint of the output image plane for the image,
wherein for each surface in the fused 3D imaging data that the ray intersects, a surface shader is computed from volume features at a point of surface intersection and added for that pixel and viewpoint of the output image plane for the image.

19. A method comprising:
receiving 3D imaging data and 2D color imaging data of a region of interest;
segmenting the 3D imaging data to identify anatomical features in the region of interest, including surfaces of the anatomical features and a corresponding volume of the anatomical features;
generating an image by fusing the 2D color imaging data to the 3D imaging data according to the surfaces, the corresponding volumes, and identities of the anatomical features; and
rendering a final image at an output image plane by casting a ray through a fused 3D imaging data of the image generated by fusing the 2D color imaging data to the 3D imaging data for each pixel and viewpoint of the output image plane for the image and assigning a color value for that pixel and viewpoint based on the 2D color imaging data.

20. A method comprising:
receiving 3D imaging data and 2D color imaging data of a region of interest;
segmenting the 3D imaging data to identify anatomical features in the region of interest, including surfaces of the anatomical features and a corresponding volume of the anatomical features;
generating an image by fusing the 2D color imaging data to the 3D imaging data according to the surfaces, the corresponding volumes, and identities of the anatomical features;
creating a projection or transform of at least one anatomical feature of the anatomical features from a fused 3D imaging data of the image generated by fusing the 2D color imaging data to the 3D imaging data; and
reprojecting a result of the projection or the transform back into the volume of the at least one anatomical feature to visualize the anatomical feature in a corresponding portion of the generated image.

* * * * *